United States Patent [19]
Weckerle et al.

[11] Patent Number: 5,747,751
[45] Date of Patent: May 5, 1998

[54] DISPOSABLE COVER FOR STETHOSCOPE HEAD

[76] Inventors: Judith C. Weckerle, 4711 Rolling Wood Dr., Durham, N.C. 27713; Kathleen L. Weaver, 110 Mel Oaks Dr., Chapel Hill, N.C. 27516

[21] Appl. No.: 760,185

[22] Filed: Dec. 4, 1996

[51] Int. Cl.⁶ .............................. A61B 7/02; A61B 19/02
[52] U.S. Cl. .................................... 181/131; 128/715
[58] Field of Search ........................ 181/131, 137; 381/67; 128/715, 773

[56] References Cited

U.S. PATENT DOCUMENTS

| | | |
|---|---|---|
| 3,255,841 | 6/1966 | Hasbrouck. |
| 4,461,368 | 7/1984 | Plourde ........................... 181/131 |
| 5,365,023 | 11/1994 | Lawton ........................... 181/131 |
| 5,428,193 | 6/1995 | Mendiberg ...................... 181/131 |
| 5,466,898 | 11/1995 | Gilbert et al. ................... 181/131 |
| 5,486,659 | 1/1996 | Rosenbush ...................... 181/131 |
| 5,564,431 | 10/1996 | Seward ............................ 128/715 |

*Primary Examiner*—Khanh Dang
*Attorney, Agent, or Firm*—Olive & Olive, P.A.

[57] ABSTRACT

A disposable cover is provided for a stethoscope head to prevent the spread of harmful organisms, bacteria and viruses between patients resulting from use of a stethoscope. The cover is formed from a substantially thin, impervious, flexible, stretchable sound transmitting sheet material, as a seamless casing with an open end wide enough to permit introduction of the stethoscope head into the casing; an opposite closed end and an intermediate neck section of reduced size and shaped so is to be able to receive the stethoscope head. The cover is essentially universal and accommodates most stethoscope styles heads as currently used. Variations of the cover relate to the shape of the cover and to the manner in which the open end is formed.

6 Claims, 1 Drawing Sheet

DISPOSABLE COVER FOR STETHOSCOPE HEAD

BACKGROUND OF THE INVENTION

1. Field of the Invention

This invention relates to a disposable cover for enveloping the head of a stethoscope to prevent the transmission of body fluids and organisms from one patient to another.

2. Description of the Related Art

In the medical field, health care personnel use the stethoscope extensively. A stethoscope head has a diaphragm portion, the surface of which is generally placed in contact with the skin of the patient. Some types of stethoscope heads only have a diaphragm portion, while others have a diaphragm portion on one side and a bell portion on the opposite side. In this description, reference to a stethoscope head refers to both stethoscope head styles. An element of the uniqueness of the invention is its suitability for both styles of stethoscope heads.

The head of the stethoscope is placed in contact with a patient's skin to listen to heart sounds, respirations and bowel sounds and to determine blood pressure. The skin surface contacted by the stethoscope head may be broken or open due to a variety of causes: surgical incision, weeping dermatitis, infected lesion, rash, abrasion, laceration, puncture wound, needle sticks, open and infected wounds and various tubes, drains, ostomies, topical irritation, micro-cuts and skin breakdown. Typical drainage from such broken skin surfaces contains blood, ostomy drainage containing blood, infected wound with abscess drainage, pleural fluid from chest tubes, peritoneal fluid from a peritoneal catheter, exudate from a lesion or rash, and blood from urinary drainage or gastric secretions. Such broken skin surfaces are potential exit and entrance sites for organisms, bacteria, and viruses, collectively referred to as foreign matter. For example, the stethoscope head comes in contact with a patient's antecubital area when the patient's blood pressure is being taken and this area is also the common site for drawing blood and obtaining intravenous access, typically leaving an open puncture wound that is likely to bleed and leave blood on the skin surface. These types of abnormal skin surface conditions occur in significant numbers in a hospital setting.

Medical personnel typically use their own personal stethoscope to examine patients. Examinations are conducted on multiple patients without disinfecting the stethoscope head between use on patients. Such examinations often involve contact of the stethoscope head with open wounds. This practice introduces the tremendous risk of transmitting harmful substances from one patient to another, including the transmission of micro-organisms such as the human immunodeficiency virus (HIV), hepatitis B (HBV), antibiotic-resistant organisms, viruses, and fungi which are often present in body fluids. The antibiotic-resistant organisms can cause serious infections in a hospital setting and require contact isolation and aggressive treatment to prevent the spread of the organisms. Examples of such antibiotic-resistant organisms are ceftazidime-resistant klebsiella pneumonia, vancomycin-resistant enterococci, methicillin-resistant staphylococci, ciprofloxin-resistant pseudomonas aueroginosa, gentamicin-resistant pseudomonas aueroginosa, and penicillin-resistant pneumococci. The type of antibiotic-resistant organism which exists may vary from one health care setting to another. However, one important way to break the cycle of transmission of such organisms from one patient to another is to ensure that body fluids from one patient's broken skin surface, e.g. an incision, are not carried to another patient.

Studies have indicated that the incidence of hospital-acquired infections and antibiotic-resistant organisms is rising nationally. [See: "Stethoscopes: A Potential Vector Of Infection?", Annals Of Emergency Medicine, Chapter 26:3, September, 1995, pages 296–299, Jeffrey S. Jones, MD, FACEP et al; and "Direct Observations Of Surgical Wound Infections At A Comprehensive Cancer Center", Archives Of Surgery, Volume 130, October, 1995, pages 1042–1047, Gerald R. Barber, R.Ph., MPH, CIC et al.] Transmission of infectious fluids can be by direct or indirect contact. Direct contact involves the transmission from the source of the infection to another person. Indirect contact can occur from the source of infection which is contacted by an object which then is placed in contact with another person who is potentially infected thereby.

The Center For Disease Control (CDC) established a set of "Universal Precautions" in 1987 to address the problem of the spread of infections diseases in health care settings specifically to prevent the parenteral, mucous membrane and broken skin exposures to blood-borne pathogens. These Universal Precautions are practiced in hospitals across the country. The Universal Precautions are recommended for all patients, regardless of their blood-borne infection status. It is recommended that health care personnel treat all patients as potentially infectious of HIV, HBV and other blood-borne pathogens, such as the antibiotic-resistant organisms named above. Health care personnel are also urged to apply the Universal Precautions to care related to blood, body tissues, semen, vaginal secretions, cerebrospinal fluid, pleural fluid, peritoneal fluid, amniotic fluid, pericardial fluid, weeping dermatitis, exudative lesions, and any fluid such as urine, feces, or emesis containing visible blood.

The Universal Precautions encourage the use of protective covers such as gloves, masks, gowns and protective eyewear to reduce the risk of exposure to potentially infective materials. These devices are primarily directed to protecting the health care personnel from the patient, and the patient from the health care worker. Neither of these devices nor the Precautions expressly address the need to prevent the transmission of infection from one patient to another.

Sanitation of devices is recommended in the prevention of transmission of infectious fluids. However, sanitation of the stethoscope is neither addressed nor practiced. Although stethoscope use presents a highly substantial risk of the transmission of infectious fluids from one patient to another, the guidelines are virtually silent with respect to proper stethoscope usage in relation to the prevention of transmission of infectious fluids. Additionally, medical personnel and patients appear unconcerned about this potential risk.

There is thus a need in the medical field for an easy and convenient to use device which assists in the prevention of the transmission of infection by means of the stethoscope head. In medical settings it is often important to apply the stethoscope quickly; therefore, the device should be easy and convenient to apply to the stethoscope.

Attempts have been previously made to create a protective cover for a stethoscope head. Prior stethoscope head covers do not however adequately address this pressing need. Such devices include: "Disposable Stethoscope Head Shield" of Turner, U.S. Pat. No. 4,871,046; "Sanitary Stethoscope" of Ulert, U.S. Pat. No. 4,867,268; "Stethoscope Bell Cover" of Hasbrouck, U.S. Pat. No. 3,225,841; "Stethoscope Securing Pad" of Taylor et al., U.S. Pat. No. 4,401,125; and "Stethoscope Cover" of Kendall et al., U.S.

Pat. No. 5,269,314. Each of these known devices provides a covering for only one portion of the stethoscope head, and leaves too much of the stethoscope head uncovered and exposed for potential contact with infectious fluids. Additionally, these devices would be difficult to apply quickly in an emergency setting.

It is therefore an object of the present invention to provide a device which assists in the prevention of transmission of infectious fluids by the stethoscope head.

A further object of the invention is to provide a cover for a stethoscope head which is easy and convenient to apply and use.

Other objects and advantages will be more fully apparent from the following disclosure and appended claims.

SUMMARY OF THE INVENTION

The present invention is directed to a disposable cover for a stethoscope head to assist in preventing the spread of foreign matter resulting from stethoscope use. The cover of the present invention comprises a seamless casing formed from a flexible, stretchable sheet material. In a first embodiment, the cover has an open end wide enough to readily permit introduction of the stethoscope head into the casing; a tapered section which is smaller in width than the width of the open end; and a receiving section whose width is sufficient to receive and envelope the stethoscope head. In a second embodiment, the cover is configured basically as a closed end tube of uniform diameter sufficient to snugly, but easily, fit over the stethoscope head. In either embodiment of the cover of the invention, the open end may be defined by a rolled edge. In an alternative to the rolled end, the open end of the cover is defined by an extended tab formed around half of the circumference of the open end. The cover of the invention is unique in that it can accommodate most stethoscope styles commonly used.

DETAILED DESCRIPTION OF THE INVENTION AND PREFERRED EMBODIMENTS THEREOF

Figure 1:
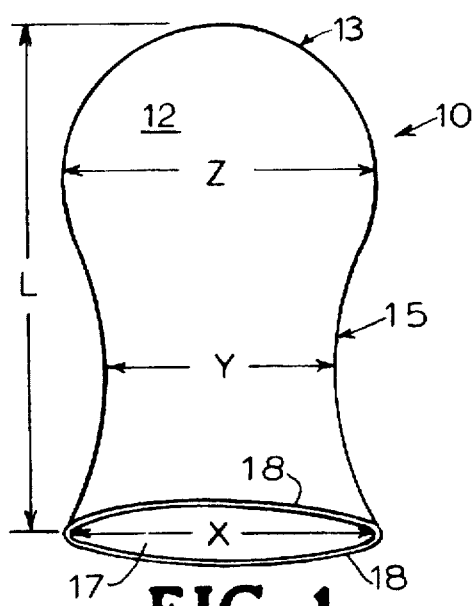
FIG. 1 is a top perspective view of a disposable cover for a stethoscope head in a first embodiment of the invention.

Referring to the figures, disposable cover 10 of the invention is generally configured as a seamless casing for receiving and enveloping a stethoscope head. Stethoscope 20, shown in dashed lines in FIGS. 2, 3 and 5, comprises stethoscope head 22 and stem 28 extending from stethoscope head 22 to connect stethoscope head 22 to sound conveying tubing 30. Tubing 30 extends from stethoscope head 22 to the ear pieces, not shown. Stethoscope head 22 comprises bell portion 24 and diaphragm portion 26 which are oriented with their common axis perpendicular to stem 28. Some stethoscope styles have only diaphragm portion 26 and not a bell portion. The invention cover, so far as applicants are aware, provides a universal cover for all style stethoscope heads commonly used. Typical stethoscope heads are approximately 4 cm to 5 cm in diameter D (FIG. 3), and can vary in thickness T from 2 cm to 4 cm. As will be seen from the description and drawings, cover 10 is able to accommodate to the varying size and style of stethoscope heads, and at the same time provides a device which is easy to apply to and remove from the stethoscope head.

Figure 3:
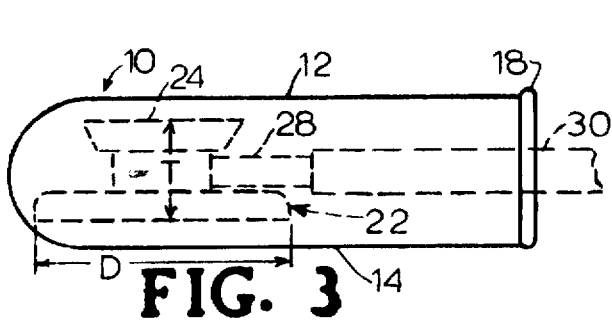
FIG. 3 is a side elevation view of the apparatus of FIG. 2.
Figure 5:
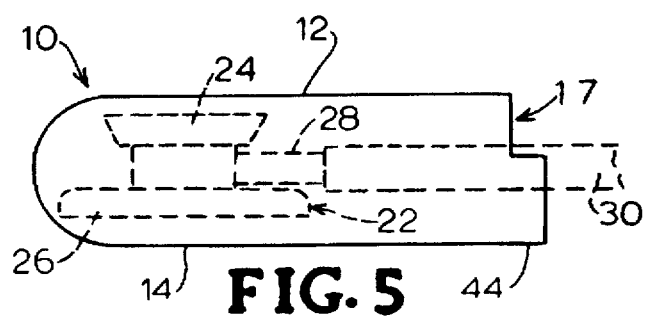
FIG. 5 is a side elevation view of the invention cover of FIG. 4 with a stethoscope head, indicated by dashed lines, shown inserted into the cover.

Disposable cover 10 of the invention is formed as a seamless casing from a flexible and stretchable sheet material. It is a particular advantage that cover 10 is seamless, as shown in FIGS. 3 and 5. As a result, cover 10 is comfortable to the patient and assists in the ease and effectiveness of use. Potential sites for breakage in cover 10 as might be provided by seams which would allow foreign matter to come in contact with stethoscope head 22 are avoided.

Figure 2:
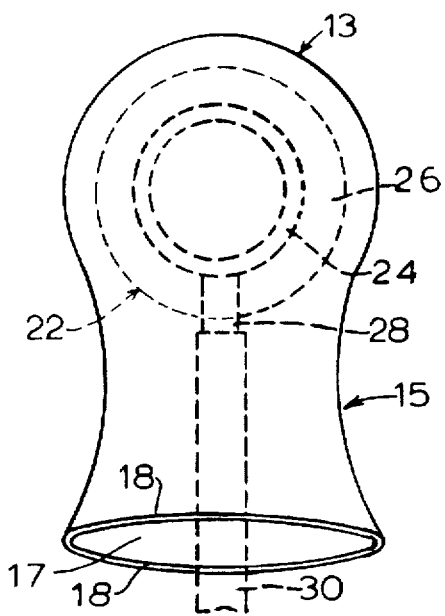
FIG. 2 is a top perspective view of the cover of FIG. 1 with a stethoscope head illustrated in dashed lines shown inserted into the cover.
Figure 4:
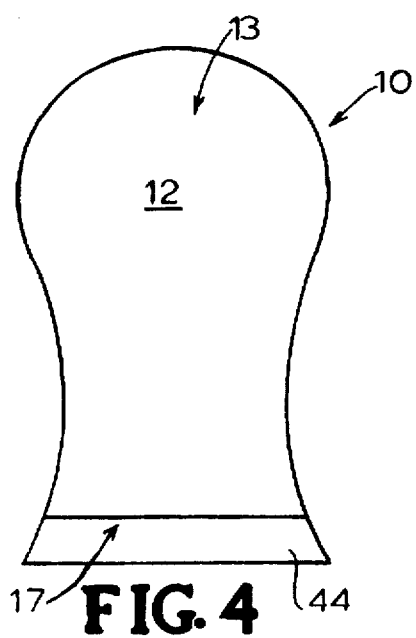
FIG. 4 is a top plan view of a variation of the first embodiment of the invention as shown in FIG. 1.

In the first embodiment, illustrated in FIGS. 1, 2 and 4, cover 10 has receiving section 13, tapered neck section 15, and open end 17. Cover 10 narrows in width from open end 17 to tapered neck section 15 and widens to receiving section 13, which includes a smooth, closed end 19. While the exact measurements for stethoscope heads vary, cover 10 is adapted to accommodate to permit such variations. Generally, the width X of open end 17 is large enough to permit stethoscope head 22 to be inserted without stretching the sheet material, and the width Y of neck section 15 is slightly smaller than diameter D (FIG. 3) of stethoscope head 22 so as to prevent cover 10 from sliding off accidentally. The distance N locates the narrow width Y such that the narrowed part of neck section 15 is spaced slightly more than diameter D from the closed end 19. Width Z of receiving section 13 at least slightly exceeds diameter D and is of a size to enclose stethoscope head 22. Length L of cover 10 is sufficient to cover stethoscope head 22 beyond its juncture with tubing 30.

In a variation of the invention, open end 17 is partly bordered by extended tab 44, as shown in FIGS. 4 and 5. Extended tab 44 helps define open end 17, and assists a user in applying cover 10 to stethoscope head 22. Tab 44 extends approximately 1 cm beyond open end 17 around approximately half of the circumference of open end 17. Extended tab 44 may be provided on either the first or the second embodiment of the invention.

Figure 6:
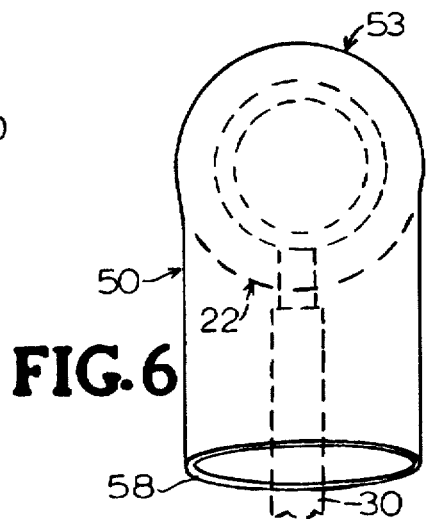
FIG. 6 is a top perspective view of a disposable cover for a stethoscope head according to a second embodiment of the invention.

In a second embodiment (illustrated in FIG. 6), cover 50 is formed in a substantially tubular configuration of a width sufficient to snugly receive stethoscope head 22 and not slip off accidentally. The illustrations of FIGS. 3 and 5 are applicable to this second embodiment of the invention as well as to the first embodiment with respect to the open end. This second configuration, with a rolled edge 58 or an extended tab 44 (as shown in FIGS. 4 and 5), is offered as being more economical to manufacture than the first embodiment and equally effective for its intended purpose.

The material currently used in the manufacture of surgical gloves, for example latex or vinyl, is suitable for forming cover 10 as a flexible, sound transmitting stretchable sheet which is impervious to body fluids. Such materials are currently approved by the Federal Food and Drug Administration for medical use, and would therefore be suitable for cover 10 of the invention. A suitable material for cover 10 of the invention is presently used for surgical gloves which are available from Maxxim Medical of Clearwater, Fla. This type material comprises a polyvinyl chloride polymer with a thickness of 0.05 mm and a minimum tensile strength of 1300 p.s.i. The material may be dusted with absorbable dusting powder, such as cornstarch. Another suitable material is a 0.06 mm thick latex sheet of the type used in Perry (TM) Powdered X-AM (R) gloves which are available from Ansell Perry, Inc. of Massillon, Ohio.

In use, stethoscope head 22 is inserted into open end 17. Edge 18 is pulled by the user over stethoscope head 22. Open end 17 is formed and maintained in a slightly open, generally circular, condition by a reinforcing rolled edge 18. The ability of cover 10 to stretch, if necessary, to receive stethoscope head 22, and its ability to retract after being stretched, to regain its original size, enables cover 10 to remain on stethoscope head 22 during use. Cover 10 is also formed such that it does not easily fall off of stethoscope head 22 during use and yet is large enough to permit stethoscope head 22 to be inserted into cover 10 without difficulty. It has been discovered that use of cover 10 does not generally hinder the user's ability to use and obtain sound signals from the stethoscope.

Placement of cover 10 onto stethoscope head 22 need not be precise, and thus stethoscope head 22 may be inserted quickly and conveniently into cover 10. This feature is especially advantageous in medical emergency situations. Cover 10 is also easy and convenient to remove so that medical personnel in emergency situations may readily use the device. It is critical that the device of the invention be easy, convenient and effective. Cover 10 thus addresses the need in the medical environment for preventing the spread of harmful organisms, bacteria and viruses through stethoscope use.

In use it is rare that only one surface of the stethoscope head 22 will come in contact with harmful foreign matter. A particular advantage of cover 10 is its capability to cover the entire stethoscope head 22 and a portion of tubing 30, as shown in FIGS. 2, 3 and 5. In normal use of a stethoscope, it is likely that portions of the opposite head surface, as well as stem 28 and tubing 30 are contacted by foreign matter. Thus, if a stethoscope cover were to only provide covering to one side of stethoscope head 22, for example, either bell 24 or diaphragm 26, the probability for the unprotected portion of head 22 becoming contaminated during use would be high, and the effectiveness of the cover would be seriously undermined. Additionally, as previously stated, the ability to quickly apply cover 10 to stethoscope head 22 makes it possible for use in emergency settings requiring quick action by medical personnel, and thus makes it more likely that cover 10 will be used when needed. Were it necessary to precisely place a cover over the diaphragm portion of the stethoscope head, it might hinder use or response time of medical personnel.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A disposable cover for a stethoscope head having a round diaphragm portion of a first diameter and, optionally, a round bell portion of a second diameter which is smaller than said first diameter, and a stem extending outwardly therefrom, said disposable cover comprising:

(a) a seamless casing formed from a substantially thin, sound transmitting, flexible and stretchable sheet material which is substantially impervious to body fluids;

(b) said seamless casing having an open end of a dimension when not stretched that is sufficient to permit introduction of the stethoscope head slidingly into the casing, a tapered neck section adjacent to the open end with a narrowest dimension thereof which when not stretched is smaller than the first diameter of said diaphragm portion of the stethoscope head and a receiving section located outwardly and adjacent to the tapered neck section and of a dimension when not stretched to slidingly receive and envelope the stethoscope head, the narrowest dimension of the tapered neck section when not stretched also being smaller than the open end (c) said open end further comprising a reinforcing edge.

2. The disposable cover of claim 1, wherein the reinforcing edge comprises a rolled edge around the open end.

3. The disposable cover of claim 1, wherein the open end further comprises an extended tab formed around substantially one-half of the open end.

4. The disposable cover of claim 1, wherein said casing is configured of a length sufficient to envelope the stethoscope head beyond a point at which said stem thereof engages a sound conveying tubing.

5. The disposable cover of claim 1, wherein the open end is formed so as to assume a generally circular shape when fully open and not stretched.

6. The disposable cover of claim 1, wherein the open end is formed so as to assume a generally hemispherical shape when fully expanded and not stretched.

* * * * *

UNITED STATES PATENT AND TRADEMARK OFFICE
CERTIFICATE OF CORRECTION

PATENT NO. : 5,747,751
DATED : May 5, 1998
INVENTOR(S) : Judith C. Weckerle and Kathleen L. Weaver It is certified that error appears in the above-identified patent and that said Letters Patent is hereby corrected as shown below:

Column 2, line 65, change "3,225,841" to read --3,255,841--.

Column 4, line 20, change "1, 2, and 4" to read --1, 2, and 3--.

Column 4, line 24, delete "19".

Column 4, line 32, delete "distance N locates the narrow width Y such that the".

Column 4, line 34, delete "19".

Column 5, line 36, change "2, 3, and 5" to read --2, 3, 5, and 6--.

Claim 1, line 21, after "end" insert --; and--.

Signed and Sealed this

Twenty-first Day of July, 1998

Attest:

BRUCE LEHMAN

Attesting Officer

Commissioner of Patents and Trademarks